US006307122B1

(12) United States Patent
Epstein et al.

(10) Patent No.: US 6,307,122 B1
(45) Date of Patent: Oct. 23, 2001

(54) INFECTION OF HUMAN NEURAL XENOGRAFTS

(76) Inventors: Leon G. Epstein, 80 Council Rock Ave., Rochester, NY (US) 14610; Manuel Del Cerro, 13 Tall Acres Dr., Pittsford, NY (US) 14534; Benjamin M. Blumberg, 32 Calumet St., Rochester, NY (US) 14610

( * ) Notice: Subject to any disclaimer, the term of this patent is extended or adjusted under 35 U.S.C. 154(b) by 0 days.

(21) Appl. No.: 07/965,901

(22) Filed: Oct. 23, 1992

Related U.S. Application Data

(63) Continuation-in-part of application No. 07/786,449, filed on Nov. 1, 1991.

(51) Int. Cl.$^7$ ................................................. A01N 63/00
(52) U.S. Cl. ............................... 800/11; 800/3; 800/18; 424/9; 424/93.1
(58) Field of Search ........................... 424/9, 93, 570, 424/571, 520, 582, 578; 800/2, DIG. 2, DIG. 5

(56) References Cited

PUBLICATIONS

Cvetkovich, et al., *Proc. Natl. Acad. Sci. USA*, 89:5162–5166 (1992).
Epstein, et al., *Journal of Neural Transplantation & Plasticity*, 3:151–158.
Epstein, *Brain & Development*, 11:353–359 (1989).
Hutchins, et al., *Developmental Brain Research*, 55:95–102 (1990).
Epstein, et al., *Annals of Neurology*, 17:488–496 (1985).
Epstein, et al., *Pediatrics*, 78:678–687 (1986).
Belman, et al., *AJDC*, 142:29–35 (1988).
Michaels, et al., *Immunodeficiency Review*, 1:71–104 (1988).
Sharer, et al., *Human Pathology*, p. 760 (1985).
Epstein, et al., *Aids Research*, 1:447–454 (1984/5).
Sharer, et al., *Human Pathology*, 17:271–284 (1986).
Meyenhofer, et al., Journal of Neuropathology and Experimental Neurology, 46:474–484 (1987).
Sharer, et al., *Neuropathology and Applied Neurobiology*, 16:317–331 (1990).
Michaels, et al., *Acta Neuropathologica*, 76:373–379 (1988).
Price, et al., *Science*, 239:586–592 (1988).
Epstein, *Brain & Development*, 11:353–359 (1989).
Mintz, et al., *AJDC*, 143:771–774 (1989).
Oxtoby, In "Pediatric AIDS; the challenge of HIV infection in infants, children, and adolescents", Chapter 1, pp. 3–21, Ed. P. Pizzo & C.M. Wilfert (1991).
Ryder, et al., *The New England Journal of Medicine*, 320:1637–1642 (1989).
Jovaisas, et al., *The Lancet*, Nov. 16, p. 1129 (1985).
Sprecher, et al., *The Lancet*, Aug. 2, pp. 288–289 (1986).
LaPointe, et al., *The New England Journal of Medicine*, 312:1325–1326 (1985).
Lewis, et al., *The Lancet*, 335:565–568 (1990).
Lyman, et al., *AIDS*, 4:917–920 (1990).
Chin, *The Lancet*, 336:221–224 (1990).
Sharer, et al., *J. Med. Primatol.*, 20:211–217 (1991).
Dreyer, et al., *Science*, 248:364–367 (1990).
Watkins, et al., *Science*, 249:549–553 (1990).
Dewhurst, et al., *Journal of Virology*, 61:3774–3782 (1987).
Clapham, et al., *Nature*, 337:368–370 (1989).
Harouse, et al., *Journal of Virology*, 63:2527–2533 (1989).
Sharer, et al., *J. Neurophathol. Exp. Neurol.*, 50:325 (1991).
Lyman, et al., *AIDS*, 4:917–920 (1990).
Letvin, et al., *Science*, 230:71–73 (1985).
Narayan, et al., *J. gen. Virol.*, 70:1617–1639 (1989).
Cheng–Mayer, et al., *Proc. Natl. Acad. Sci. USA*, 86:8575–8579 (1989).
Gendelman, et al., *Journal of Virology*, 58:67–74 (1986).
del Cerro, et al., *Neuroscience*, 21:707–723 (1987).
del Cerro, et al., *Invest. Opthalmol. Vis. Sci.*, 32:763 (1991).
Boom, et al., *Journal of Clinical Microbiology*, 28:495–503 (1990).
Saiki, et al., *Nature*, 324:163–166 (1986).
Morrow, et al., *J. gen. Virol.*, 68:2253–2257 (1987).
Spertzel, et al., *Antiviral Research*, 12:223–230 (1989).
del Cerro, In "Progress in Retinal Research", 9:230–272 (1989).
del Cerro, et al., *Brain Research*, 574:1–8 (1992).
McCune, *Virology*, 1:229–235 (1990).

*Primary Examiner*—Karen M. Hauda
*Assistant Examiner*—Peter Paras, Jr.
(74) *Attorney, Agent, or Firm*—Flehr, Hohbach, Test, Albritton & Herbert

(57) ABSTRACT

Immunocompromised or immunosuppressed non-primate chimeric mammalian hosts comprising a neuronal graft in the eye are provided for studying various events associated with humans. Particularly, the chimeric host may have solely human fetal neuronal xenografts or other fetal xenografts with other tissue, where the various tissues may be studied as to their response to a variety of agents, their response to pathogens or other diseased states, or their response to agents for the treatment of the various indications.

20 Claims, No Drawings

INFECTION OF HUMAN NEURAL XENOGRAFTS

CROSS-REFERENCE TO RELATED APPLICATIONS

This application is a continuation-in-part of application Ser. No. 07/786,449, filed Nov. 1, 1991.

CROSS-REFERENCE TO GOVERNMENT GRANTS

Research in support of the subject invention was supported to PHS Grants NS28754, EY09217 and AI32315. The United States Government may have rights in this invention.

TECHNICAL FIELD

The field of this invention is the use of human neural human xenografts in the eye of an immunocompromised host for studying the effect of various agents on human neural tissue.

BACKGROUND

In the attempts to understand human disease and develop therapies, the medical and associated fields have frequently relied upon analogies to observations in animals. While there are a number of similarities between non-primates and primates, there are also a large number of differences. Many of the naturally-produced agents, such as cytokines, hormones, surface membrane proteins, blood proteins, and the like, differ significantly in their composition. Most importantly, for the transduction of signals, cellular interactions, regeneration and differentiation, the molecules involved frequently have a narrow range of host specificity. Where autocrine or paracrine mechanisms are not involved, xenogeneic tissue introduced into a non-primate host must totally rely upon the host for the source of ligands not produced by the xenogeneic tissue or other xenogeneic tissue must be supplied which makes such ligands available. Furthermore, xenogeneic tissue is subject to rejection by an immunocompetent host, so that means must be provided to protect the xenogeneic tissue from degeneration as a result of immune rejection. There are no viable hosts which have no protective mechanisms against foreign entities.

There has been substantial interest in using immunosuppressive agents or immunocompromised hosts to extend the period in which xenogeneic explants may be maintained as viable functional tissue. Frequently, in order to be useful to study the effect of the agents on the xenogeneic tissue, the tissue must retain most if not substantially all of its natural characteristics. However, since the xenogeneic tissue, at best, is only a very small amount of tissue compared to the entire host, it can be subject to many modifications which may change its characteristics, so as to substantially reduce its predictive capability as to the response of the xenogeneic host.

Where the xenogeneic tissue has mobile cells, such as host organs of peripheral blood lymphocytes, such as lymph nodes, thymus, spleen, pancreas, tonsils and the like, these cells may be rapidly displaced by the xenogeneic host cells. Furthermore, vascularization and lymphatic connection can result in the xenogeneic tissue being invaded by host endothelial cells which provide the vessels. Other host cells may also invade the tissue, so as to change the characteristics of the tissue. It is therefore not sufficient that the tissue remain viable or even grow, it is necessary that the tissue retain a substantial degree of similarity to the native tissue, so as to provide responses which are predictive of the responses of the native tissue in the source host for the xenogeneic tissue.

Humans as a host are particularly unique, in the many restrictions which apply to humans and the manner in which they may be studied. Normally, one cannot induce a disease in a human to study the etiology of the disease. Nor can one treat a human with an agent, without first having gone through extensive tests with other mammals, to determine efficacy and pharmacological properties. With many diseases, there are many infectious agents which are tropic for human tissue. In other pathologic conditions, human tissue may respond quite differently from other hosts, due to the nature of its surface membrane proteins, particularly as to metabolic pathways, pharmacology, and the like.

It is therefore of substantial interest that mammalian hosts, particularly small mammalian hosts, be developed, which allow for the study of the response of human tissue to a variety of agents, particularly pathogenic agents and therapeutic agents used to treat the infection or diseased state.

RELEVANT LITERATURE van Dooremaal, *Utrechsche Loogeschool*, (1873); 3, 277–290 lodged cells from human-labial mucosum and other rather unlikely explants in the rabbit anterior chamber. Explanted fetal retina, both allo- and xenotrans-plantation, in the study of retinal plasticity in the rat anterior chamber has been reported by del Cerro, M., *Retinal transplants*. In: Osborne, N., Chader, J., eds, *Progress in Retinal Research*. Vol. 9, Oxford, Pergamon Press, 1989;230–272; Royo and Quay, Growth (1959); 23, 313–336; del Cerro, M., et al., Invest. Ophthalmol. *Vis. Sci.* (1984); 25, 62(abstr.); del Cerro, M., et al. ibid. (1985); 26, 1182–1185; del Cerro, M., et al., Neuroscience (1987); 21, 707–724; and Medawar, *Br. J. Exp. Pathol.* (1984); 29, 58–69. Extensive research has been conducted in the area of syngeneic and xenogeneic grafting of CNS tissue, especially in the study of mechanisms of human brain development. Olson, et al., *Prog. Brain Res.* (1988); 78, 583–590, grafted several areas of 8–11 week gestation human fetal brain and spinal cord into the anterior chamber of nude mice, nude rats and rats immunosuppressed with cyclosporin A. First trimester human cerebellar and cerebral cortex, and hippocampus and spinal cord xenografts appear to develop histologically according to a human timetable. Anchen, et al., *Exp. Brain Res.* (1989); 75(2), 317–326; Bickford-Wimer, et al., *Proc. Natl. Acad. Sci. USA* (1987); 84(16), 5957–5961; and Granholm, et al., *Exp. Neurol.* (1989); 104, 162–171. Host transplantation survival of first trimester human CNS and retina xenografts have been reported to be as long as 200 days. Aramant, et al., *Restorat. Neurol. Neuro. Sci.* (1990); 2, 9–22.

Epstein, et al., *J. Neural Transplantation and Plasticity* (1992); 3, 151–158 report xenografts of second trimester human fetal brain and retinal tissue in the anterior chamber of the eye of immunosuppressed rats. Cvetkovich, et al., *Proc. Natl. Acad. Sci. USA* (1992); 89, 5162–5166 describe human immunodeficiency virus-type one infection of neural xenografts. The SCID-hu mouse has been reported as a model system for study of HIV-1 infection of human cells. McCune, et al., *Science* (1988); 241, 1632–1639.

SUMMARY OF THE INVENTION

Methods and non-primate animals are provided for the study of agents on neural tissue and the blood/brain barrier.

Human retinal and/or CNS tissue is implanted into the anterior chamber or subretinal space of the eye of an immunocompromised non-primate mammalian host and allowed to become established. The neuronal tissue may then be subjected to a variety of agents by various means depending upon the agent and the tissue observed or removed and analyzed. Of particular interest as agents are disease-causing agents, e.g., pathogens which are tropic for human neural tissue, and the drugs used to treat the pathology.

DESCRIPTION OF THE SPECIFIC EMBODIMENTS

In accordance with the subject invention, novel chimeric hosts and their use are provided, where the chimeric hosts are characterized by having xenogeneic viable functional neuronal tissue in at least one eye, being immunocompromised, as a result of an immunosuppressive drug or regimen or a genetic lesion, and wherein said xenogeneic tissue may be subjected to an agent tropic for said xenogeneic tissue but not tropic for said host. Usually, the implant will be normal tissue, but may include diseased tissue.

The implants which are introduced into the eye will normally comprise primate, particularly human, retinal or brain tissue, more particularly fetal tissue, of the first and second trimester, for some applications preferably the second trimester, where the first trimester is up to about 11 weeks, and the second trimester is from about 12–24 weeks, particularly 12–20 weeks.

The brain regions of interest are particularly the telencephalon, including full thickness cortical mantle with ventricular surface or intact retina, or fragments thereof. The brain region comprises neuronal, macroglial and microglial elements. The retina tissue will generally be dissected free of other structures in the eye and may be mechanically or enzymatically dissociated. Normally, the tissue fragments will be from about 0.2–5 mm, more usually from about 0.5–2 mm. The fragments may be administered to the eye of the host by means of a needle and injection into the anterior chamber or subretinal space of the eye. (See del Cerro, et al., Neuroscience (1987); 21, 707–724; del Cerro, Retinal Transplants In: *Progress in Retinal Research*, supra and del Cerro, et al., Intraocular Xenografts of Human Petal Retina and Brain:

An Experimental Target for the AIDS Virus; *Invest. Opthalmol. Vis. Sci.*, Annual Meeting, Sarasota, Fla., Apr. 28–May 7, 1991, p. 763)

The implants are able to function for long periods of time, usually in excess of 2 weeks, more usually in excess of 4 weeks, and may function for 6 weeks or more.

The host may be any convenient non-primate mammal, particularly a small laboratory mammal. Hosts may include murine, lagomorpha, feline, canine, ovine, bovine, equine, porcine, etc. They will usually be 3–6 mos. of age for smaller mammals, e.g., rodentiae. Of particular interest is rodentiae, particularly mice and rats. The animals which are used may be immunocompetent, but immunosuppressed, or immunoincompetent. By immuno-suppressed or immunoincompetent is intended that the host substantially lacks a functioning lymphoid system, although other hematopoietic lineages may also be debilitated or inactive, such as granulocytes and/or monocytes, and particular subsets thereof. For immunosuppression, various drugs are available, such as cyclosporin A, dexamethasone, steroids, FK506, cyclophosphamide, etc. Dosage will be the normal dose range for the particular host, e.g., cyclosporin A for rats will be in the range of about 2–15 mg/kg/day.

Naturally-occurring hosts can be immunocompetent or made so by mutation, particularly homologous recombination. Defects in the lymphoid lineage can be achieved in a variety of ways, by having a defective thymus or lacking a thymus all together, by having a defective recombination system, which can be as a result of a lesion in a regulatory gene regulating recombination function, e.g., expression of a recombinase, such as the RAG-1 and -2 genes, lack of expression of certain cytokines, e.g., IL-2–8, IL-10, etc., lack of expression of surface membrane receptors or antigens, e.g., kit, MHC, T-cell receptors, sIg, CD4 and/or CD8, CD3, CD27, CD40, cell adhesion molecules, e.g. L-selectin, LFA-1, and the like. Various naturally-occurring mammals which are immunoincompetant are available, such as athymic (nude) mice and rats, C.B.17 scid/scid mice, scid horses, congenic mice mated with C.D.17 scid/scid mice, etc.

Alternatively, by use of homologous recombination, particularly with mice, where lesions may be introduced into embryonic stem cells, one can introduce one or more lesions into genes associated with the recombination system or introduce lesions into the loci of the T-cell receptor, MHC, either or both Class I and Class II, and/or immunoglobulin loci to inhibit lymphoid maturation.

Of particular interest are hosts which include primate tissue, particularly fetal tissue, other than the neuronal tissue in the eye of the host. Thus, other tissue may include hematopoietic, stromal, lung, fibroblasts, epithelium, endothelium, stem cells, or other cells associated with particular solid organs, such as bone marrow, pancreas, appendix, tonsil, gut, lung, kidney, GALT (gut-associated lymphoid tissue), MALT (mucosal-associated lymphoid tissue), tongue, mucosal tissue, adrenal gland, thymus, liver, thyroid, pituitary gland, hypothalamus, bone, including osteoclasts and osteoblasts, muscle, including myoblasts and myocytes, and the like. Various cell lineages may be of interest, such as macrophages, other monocytic cells, etc.

Other tissue which may also be included includes a combination of thymus and liver, where the two are contiguous and produce what has been referred to as bone marrow equivalent. That is, the histology indicates that the cellular population of bone marrow appears to be present in a thymic stromal environment. See Namikawa, et al., *J. Exp. Med.* 172, 1055 (1990).

The tissue may be present for a variety of reasons, such as providing for hematopoietic cells of the same species as the xenogeneic tissue in the eye, where the hematopoietic cells may include B-cells, T-cells, monocytes, e.g., macrophages, neutrophils, basophils, and eosinophils, granulocytes, mast cells, megakaryocytes, erythrocytes, precursor cells for microglia, and the like. Particularly, with hematopoietic cells, one may add specific cell subsets, such as T-cell subsets, more particularly subsets having particular variable regions of the α, β, δ, or γ subunits, where the polymorphic regions are suspected or have been shown to be associated with susceptibility to a particular neuronal disease.

Alternatively, one may be interested in determining the effect of cells from various tissues, such as bone marrow, epithelial cells, endothelial cells, or the like where the tissue may be diseased, e.g., neoplastic, or may be infected with a pathogen. In this manner, one can not only investigate the effect on neuronal tissue of other diseased tissue from the same species, but may also investigate the effect on neuronal tissue of various agents used for the treatment of the other diseased tissue.

In many instances, infection of cells other than neural cells, can lead to various diseases. For example, in the case of HIV-1, it is found that infection with HIV blood leads to neuronal damage, where blood cells (macrophages) invade the brain and primary infection of brain microglia or other neural cells may occur. Other viruses, such as Herpes simplex virus, cytomegalovirus, Rabies virus, CMV, EBV, Herpes zoster, measles virus/LTV, JC, polio borna have been reported to be associated with neuronal damage. Other agents affecting the brain include substances from prion diseases. T-cells with particular Vβ and/or Vα regions have been reported to be involved in the etiology of multiple sclerosis, and may be involved in Alzheimer's disease, senile dementiae, motor neuron disease, spinal muscular atrophy, myasthenia gravis, ALS, etc.

Of particular interest is the study of agents which may be used to act on various tissues, particularly diseased tissues, particularly for therapeutic purposes on tissues other than neuronal tissue. By having xenogeneic tissue from the same species, both the neuronal tissue in the eye and the other tissue at a different site, one can not only determine the effect of an agent or pathogen or other indication on the other tissue, but also the effect on the neuronal tissue at the same time.

The tissue other than neural tissue may be introduced at any convenient site in the host. Convenient sites include mammary fat pad, kidney capsule, peritoneal capsule, subcutaneous, popliteal fossa, pancreas, and the like.

The various agents which may be involved with the various tissues included in the immunocompromised host may be drugs, pathogens, toxins, or the like. Furthermore, the other tissue which is introduced, may be normal or abnormal tissue, particularly neoplastic tissue. Where neoplastic tissue is employed, one has the opportunity to determine the effectiveness and therapeutic range of a chemotherapeutic agent, as well as its effect on neuronal tissue. Thus, by introducing xenogeneic neoplastic tissue into normal host xenogeneic tissue of the same species, so as to provide a relatively normal environment for the neoplastic tissue, one can improve the ability of the neoplastic tissue to grow in the foreign host and enhance the predictiveness of the effectiveness of the chemotherapeutic agent.

Similarly, one may introduce tissue for which a particular virus or pathogen is tropic, such as lymphoid or mucosal tissue for cytomegalovirus or gut or intestinal tissue for *H. pylori*, etc. One may then screen various agents for therapeutic effect and therapeutic dosage, while at the same time investigating the effect of the agent on the neuronal tissue.

In addition, one may introduce neural tissue into the eye, where the neural tissue may be infected at or before the time of introduction or subsequent to the introduction by injection with the pathogen. One may then investigate the ability of various agents to infiltrate into the neural tissue, as well as the effect of the pathogen on the neural tissue. Where various cells have a pathogenic effect on neural tissue, such as certain T-cells or monocytes, these T-cells or monocytes may be introduced into the host or directly into the neural tissue and the effect of the T-cells on monocytes or the neural tissue investigated, as well as the effect of various agents in modulating the T-cell or monocytic role. Thus, the subject chimeric models provide for the opportunity to investigate a wide variety of diseases, agents and mechanisms associated with etiology of disease, as well as the therapy of the diseases, including pathogenic, neoplastic and autoimmune diseases.

In substantial part, because of the significance and seriousness of HIV, and its effect on the brain, the subject chimeric host provides for a useful animal model for investigating the etiology of the neuropathology of HIV. Furthermore, since the tissue is fetal, one may study the vulnerability and timing of intrauterine HIV infection.

To study HIV infection, human neural fetal tissue may be introduced into the anterior chamber or subretinal space of the host's eye. Conveniently, the introduction may be by syringe using an appropriate-gauge needle which can handle the size of the tissue. The tissue will normally be introduced as fragments, rather than dispersed cells. The tissue grows and becomes vascularized, where the grafts form spherical or oblong masses with well-defined limits and a characteristic pearlish glow on their surface. Light- and electron-microscopic observations demonstrate that neuroblastic cells and neuronal precursors continue their growth and differentiation within these grafts. Ultrastructure analysis of neural grafts reveals well-defined axonal growth cones with synaptic vesicles, confirming the neuronal differentiation occurring within these grafts. The vascularized xenografts develop an intact blood/brain barrier.

Infection may be achieved in a variety of ways, by systemically-inoculated cell-free virus, by direct injection into the graft, by injection of infected human cells into the bloodstream or into the graft, by transfection with cloned viral DNA, or other convenient means. In similar manner, other pathogens may be introduced into the neuronal tissue or other tissue, as indicated previously.

The infected tissue may then be analyzed in a variety of ways. The xenogeneic tissue may be monitored directly in the eye by biomicroscopy, or after removal using techniques based on the polymerase chain reaction for identifying HIV or other pathogen, by performing an immunoassay for proteins associated with a particular pathogen, and the like. The particular manner in which the pathogen is assayed is not critical to this invention.

The following examples are offered by way of illustration and not by way of limitation.

EXPERIMENTAL

Example 1 Studies of HIV infection

The hosts for these studies were 100 to 120-day old male albino rats of 150–250 g body weight of the specific pathogen-free Sprague-Dawley strain (Charles River). The animals were housed in sterilized micro-isolator cages in a room reserved for the subject studies. The rats were immunosuppressed by daily intramuscular injection of cyclosporin A (10 mg/kg of rat).

Donor fetal tissue of gestational-age 10–17.5 weeks was obtained from elective therapeutic abortions procured with informed consent in accordance with applicable guidelines. The brain regions employed were the telencephalon including full-thickness cortical mantel with the ventricular surface, which were mechanically dissociated to 1–2 mm fragments under a dissecting microscope. The region contains neuronal, glial and microglial elements. In similar manner, the entire intact fetal retina was dissected free from other structures in the eye and mechanically dissociated. Following general and topical anesthesia, the small fragments of human fetal retinal or brain tissue were backloaded into a 50 $\mu$ Hamilton syringe and 10 $\mu$l was injected via a 27 gauge butterfly needle into the anterior chamber of the rat's eye under microscopic observation. Survival times for the tissue range from 0–91 days after transplantation.

Features of interest were photographed using a stereomicroscope with the animal under light anesthesia. Biomicroscopic observations indicated that the grafts in the anterior chamber grew and were vascularized, forming spherical or oblong masses with well-defined limits and a characteristic glow on their surfaces. Neuroblastic cell growth and differentiation was observed with light- and electron-microscopes. Ultrastructural analysis of neural grafts revealed well-defined axonal growth cones with synaptic vessels, indicating neuronal differentiation.

To demonstrate that the vascularized xenografts develop an intact blood/brain barrier, the rats were injected 250 μg/g body weight of horseradish peroxidase (Sigma Type VI). After sufficient time for distribution of the enzyme, the enzyme was found in all vascularized rat tissue, but not in the brain (other than in the area postrema). The enzyme did not penetrate the neural xenograft when examined by light and electron microscopy.

Rats with established human neural xenografts were challenged with laboratory strains of HIV-1 at $10^3$–$10^4$ TCID or with HIV-1 infected primary human monocytes, lymphocytes or human monocytic or lymphocytic cell lines. The animals were euthanized at intervals from 3–10 days after inoculation, the graft dissected free or fixed in 4% buffered paraformaldehyde. DNA was extracted (Blum, et al., *J. Clin. Microbiol.* (1990), 28, 495–503) and analysis performed by PCR using HIV-1 specific primers (Saiki, et al., *Nature* (1986), 324, 163–166) and ISH was performed using an HIV-1 specific RNA probe. The data indicated that HIV-1 DNA was present in several of the grafts and that intact cells were present expressing HIV-1 mRNA.

Example 2

The hosts for this study were 100–120-day old male Sprague-Dawley rats (Charles River) of 200–350 g body weight. They were pathogen free. The animals were housed in sterilized microisolator cages in a cubical used for the studies. They were maintained on an immunosuppressor regime utilizing cyclosporin A at a dose of 6 mg/kg i.m. one day prior to transplantation, followed by a maintenance dose of 5.0–6.0 mg/kg i.m. daily, adjusting the dose according to blood levels and serial weights. This resulted in cyclosporin A blood levels of 1000–1500 mg/ml.

Fetal tissues were procured from elective therapeutic abortions in strict accordance with scientific and ethical guidelines of the NIH and the University of Rochester. After vacuum extraction, the gestational age of the tissue was confirmed, using heel-to-toe measurements in comparison with standardized charts. Brain or retinal tissue from fetuses between 12 and 19 weeks gestation was used for these studies. The number of animals that received transplanted tissue at each gestational age were distributed as follows: 12 weeks gestation (n=24), 13 weeks gestation (n=9), 14 weeks gestation (n=11), 15 weeks gestation (n=7), 17 weeks gestation (n=16), 19 weeks gestation (n=10).

Large fragments of neural tissue were identified and collected in human plasma. The intact retina or brain regions of interest were separated under a dissecting microscope with the tissue submerged in fresh human plasma and mechanically dissociated into small (>0.5 mm$^3$) fragments using curved iris scissors. The brain region routinely used was telencephalon including both the ventricular and cortical surfaces, which includes proliferating neuronal and glial precursors.

Surgical Procedure

Small fragments of human fetal brain tissue were back-loaded into a 50 μl Hamilton syringe. Following general and topical anesthesia, 10 μp of fetal tissue suspension was injected into the anterior A chamber via a 27-gauge butterfly needle using direct observation under the dissecting microscope. Excess fluid was allowed to egress by partial removal of the injecting needle. The puncture sites were clean and self-sealing.

The progress of the transplants and the status of the eye's interior chambers were periodically monitored through the transparent cornea using direct ophthalmoscopy or under a stereomicroscope or slit lamp with photographs taken as necessary.

Histological and Immunohistochemical Studies

Animals were anesthetized with a lethal dose of pentobarbital at selected intervals after transplantation ranging from 2–35 days. Following enucleation, each eye containing a xenograft was fixed in either 4% paraformaldehyde for 2 hours at 40° C. for paraffin embedding, or in 2% glutaraldehyde in a 0.1 M cacodylate buffer (pH 7.2–7.4) for plastic embedding. Immunohisto-chemical studies were performed with avidin/biotin kits (Vector ABC) using modifications of the procedure (Hsu, et al., *Am. J. Clin. Pathol.* (1981), 75, 734–738). Primary antibodies used included anti-glial fibrillary acidic protein (bovine GFAP, DACO), and anti-PGP 9.5 (Ultraclone Limited), (Kent and Clark, *Dev. Brain Res.* [1991], 58, 147–150) to identify astrocytes and neurons respectively. Biotinylated lectin Ricinnus communis agglutinin-1 (RCA-I-lectin, Vector) (Mannogi, et al., *Acta. Neurophathologica* (1986), 71, 341–343) was used to identify microglia.

Horseradish Peroxidase Marker Studies

To test whether vascularized xenografts develop an intact blood/brain barrier, two rats with xenografts established two weeks earlier were injected via the femoral vein with horseradish peroxidase (HRP, Sigma Type VI, 25 μg/100 g body weight) with minor modifications of the protocol (Hirano, et al., *J. Neurophath. Exp. Neurol.* (1970), 29, 432–440). After 30 minutes, the animals were perfused with 2% formaldehyde/2% glutar-aldehyde in a 0.1 M cacodylate buffer (pH 7.2–7.4). Tissue sections were treated with hydrogen peroxide and diaminobenzidine to expose the peroxidase marker and prepared for ultrastructural examination (Del Cerro, *Progress in Retinal Research* (1989), supra).

Results

The overall success rate of establishing viable xenografts into rat eyes was 82% (63/77). A successful xenograft was defined as a healthy-appearing graft at 1-week post-transplantation. In all cases, enucleation was performed while the animals harbored healthy transplants. The longest surviving graft was 60 days. Grafts placed in animals without immunosuppression regressed after 7–10 days.

Biweekly ophthalmological examination revealed that healthy neural tissue grafts enlarged to form spherical or oblong masses, 1–2.5 mm in size, with well-defined limits and a characteristic pearlish-white glow present on the surfaces.

Light microscopical study of plastic embedded sections from grafted eyes confirmed and expanded the in vivo observations. Almost invariably the grafts grew attached to either the anterior iridal or the posterior corneal surfaces, with some larger grafts bridging both structures. Blood vessels were seen frequently. They appeared to be vascular outgrowths linking the graft to the host iridal vessels. In subsequent experiments, injection of colloidal carbon into the rat femoral vein demonstrated continuity of the vasculation of the rat iris and the intact graft. Electron microscopy later showed tight junctions between endothelial cells within the graft, further confirming the presence of a blood/brain (graft) barrier. The growth process continued within the grafts, as evidenced by the definite increase in total mass as well as by the presence of mitotic cells. The brain tissue grafts showed neurons characterized by finely-dispersed nuclear chromatin, one or two prominent nucleoli, and some cytoplasmic processes arising from the cell soma. A meshwork of these processes formed a neuropil separating neuronal cells from each other. Retinal grafts were characterized by the presence of conspicuous photoreceptor rosettes, with relatively large central lumina. Neural cells reminiscent of those in the inner nuclear layer of the normal retina were arranged outside the rosettes. Immunohistochemical studies identified PGP 9.5-positive neurons and GFAP positive astroglia; also, a few RCA-I positive "microglia" cells were seen. It was usual to find an absence of inflammatory cells in the host anterior chamber, a finding in agreement with the clear ocular media observed during the in vivo examinations.

Electron microscopical analysis of the grafts revealed the presence of synaptic contacts in growth cones (del Cerro and Snider, *J. Comp. Neurol.* [1968], 133, 341–362). Presence of the growth cones supports the continuous neurogenesis within the grafts. Ultrastructural identification of neuroblasts or young neurons with relatively large nuclei and scant cytoplasm was possible at this level. Although astroglial cells in a discontinuous glial ensheathment of the blood vessels were seen under the light microscope, unambiguous identification of astroglial cell bodies was not possible. It was possible to identify the electron microscopical correlates of active microglial cells in the form of macrophages containing abundant secondary lysosomes in their cytoplasm.

Studies of the Blood/Graft Barrier

After the injection of horseradish peroxidase, the tracer had penetrated other tissues but not the vascularized xenograft, supporting the conclusion that a functional blood/graft barrier was formed within the transplanted human neural tissue (see above).

Example 3 An Investigation of HIV Infection of Neural Xenografts

Transplantation of the fetal tissue was performed substantially as described in Example 2.

Preparation of HIV-1 Inoculum. Low-speed supernatants from tissue culture-grown HIV-1 (patient samples or standard reference strains) were filtered (0.2 aim pore diameter) and treated with RQ1 RNase-free DNase (Promega) at 2 $\mu$g/ml for 20–30 minutes at room temperature in the presence of 0.01 M $MgCl_2$ to eliminate carryover HIV-1 proviral DNA. Supernatants were placed in 4.0 ml ultracentrifuge tubes, underlayered with a cushion of 0.5 ml of 40% glycerol in 50 mM Hepes at pH 7.8, and centrifuged for 1 hour at 40,000 rpm at 15° C. in a Beckman SW60 rotor. The supernatant plus 0.2 ml of the glycerol solution was removed, and the pelleted virus was resuspended in the remaining 0.3 ml by gentle pipetting.

Isolation. Culture, and HIV-1 Infection of Human Monocytes. Monocytes cultured for 7 days in Teflon bottles at a density of $1 \times 10^6$ cells per ml were exposed at a multiplicity of infection of 0.01 infectious virus per target cell to monocyte-tropic HIV-1 strain ADA as previously described (Gendelman, et al., *J. Exp. Med.* [1988], 167, 1428–1441; Gendelman, et al., AIDS [1990], 4, 221–228; and Gendelman, et al., AIDS [1989], 3, 475–495). Twenty percent of these monocytes were found to be HIV-$_{ADA}$-infected by in situ hybridization in control experiments. All viral stocks were tested and found free of mycoplasma contamination (Gendelman, et al., AIDS [1990], 4, 221–228; and Gendelman, et al., AIDS (1989), 3, 475–495) (Gen-Probe II; Gen-Probe, San Diego).

HIV-1 Infection of Human Neural Xenoarafts. Animals in Group I (n=16) were experimentally inoculated by multiple routes with concentrated cell-free HIV-1 (titered to $1 \times 10^3$ to $1 \times 10^4$ tissue culture 50% infective dose [$TCID_{50}$]/ml) 7–10 days after neural xenografts were placed. Of these animals, Group IA (n=3) received $1 \times 10^3$ $TCID^{50}$ intravenously (i.v.), $5 \times 10^2$ $TCID_{50}$ intramuscularly (i.m.) and intraperitoneally (i.p.), and $7 \times 10^1$ $TCID_{50}$ intraocularly (i.o.); Group IB (n=3) animals were inoculated similarly i.m., i.p., and i.o. but not i.v.; Group IC (n=2) animals were inoculated with $2 \times 10^1$ $TCID_{50}$ intracerebrally (i.c.) and $1 \times 10^3$ $TCID_{50}$ i.m.; Group ID (n=4) animals were inoculated with $1 \times 10^4$ $TCID_{50}$ i.v.; and Group IE (n=4) animals were inoculated with $5 \times 10^3$ $TCID_{50}$ i.v. and i.m.

In Group II (n=8), concentrated HIV-1 ($1 \times 10^3$ $TCID_{50}$) was mixed with the neural tissue explant at the time of engraftment in the anterior chamber. In Group III (n=25), animals were inoculated with HIV-1$_{ADA}$-infected human monocytes ($10^4$ cells in 5 $\mu$l) mixed with 5 $\mu$l of fetal brain tissue fragments. In this experiment, 7 animals received neural tissue only bilaterally, 7 animals received neural tissue plus uninfected human monocytes, and 11 animals received neural tissue plus HIV-1$_{ADA}$-infected monocytes bilaterally. Representative animals were euthanized on post-transplantation days (PTDs) 7–14. Grafted tissue was recovered by enucleation and immediately frozen or prepared for histologic or ultrastructural studies. Grafts survived in oculo for 30 days or more; however, to assess infectibility with HIV-1, the animals were euthanized prior to this point.

In Situ Hybridization for HIV-1 mRNAs. The pBenn-6 6.5 kilobase (kb) HindIII fragment recloned in the RNA transcription vector pSP64 (Promega) was used to prepare HIV-1-specific sense and antisense RNA transcripts (Benn, et al., *Science* [1985], 230, 949–951 and Stoler, et al., *J. Am. Med. Assoc.* [1986], 256, 2360–2364). These were synthesized by using SP6 RNA polymerase and tritium-labeled UTP and CTP to a specific activity of $1.13 \times 10^8$ dpm/$\mu$g. In situ hybridization was performed as previously described (Stoler, et al., *J. Am. Med. Assoc.* [1986], 256, 2360–2364 and Sharer, et al., *Neuropathol. Appl. Neurobiol.* [1990], 16, 317–331).

PCR. DNA was extracted from tissue fragments (10–20 mg) by the method of Boom, et al., *J. Clin. Microbiol.* (1990), 28, 495–503. To identify HIV-1 in xenografts, we used nested pol (JA17, JA18, JA19, JA20) and env (JA9, JAb10, JA11, JA12) primer sets that recognize diverse HIV-1 field isolates (Albert and Fenyo, *J. Clin. Microbiol.* [1990], 28, 1560–1564). We have previously described the use of efficient primers and conditions for PCR amplification and cloning of the V3 region of HIV-1 (Epstein, et al., Virology [1991], 180, 583–590). We also used a nested primer set for the HIV-1 nef gene (outer set, starting at nucleotide 8796, 5'-TTCGCCACATACCTAGAAGAATAAGA-3'and, starting at nucleotide 9532, 5'-CCGCCCAGGCCACGCCTCCCT-3'; inner set, starting at nucleotide 8840, 5'-TTGCTATAAGATGGGTGGCAAGTG-3' and, starting at nucleotide 9498, 5'-CGGAAAGTCCCTTGTAGCAAGCTC-3'; positions are relative to the HXB2 clone of HIV). To distinguish rat from human fetal DNA, we designed a set of nested primers based on the sequences of the human and rat $D_1$ dopamine receptor genes recently published by Zhou, et al., Nature (London) (1990), 347, 76–80. These were $D_1$ human outer 5'-GTGTTTGTGTGGTTTGGGTGG-3', inner 5'-ATAACAATGGGGCCGCGATGT-3', and reverse 5'-CAGGTTGGGTGCTGACCGTTT-3'; and $D_1$ rat outer 5'-TGGTTTGGGTGGGCGAATTCT-3', inner 5'-CATTAACAACAATGGGGCTGT-3', and reverse 5'-ATGCTGTCCACTGTGTGTGACA-3'. In addition, we used the β-globin primer set (GH20/GH21 outer, PC03/PC04 inner) of Saiki, et al., Nature (London) (1986), 386, 163–166, to test the efficiency of extraction; this set identified both human and rat DNA. Results were scored as positive only if specific bands were observed with at least two primer sets for HIV-1 and one for host DNA.

The experience with the xenografts and their structural appearance was the same as described in Example 2

Histologic examination of xenografts from Group I animals (infected with cell-free HIV-1 by systemic inoculation) and Group II animals (infected with cell-free HIV-1 inoculated in oculo) did not reveal any histologic differences compared with the appearance of grafts from control animals with neural tissue not exposed to HIV-1. In Group III, the grafts were compared between animals receiving only fetal brain tissue and animals receiving brain plus uninfected human monocytes or brain plus HIV-$1_{ADA}$ infected monocytes at 7 and 14 days after inoculation. Grafts composed of neural tissue only, or neural tissue and uninfected monocytes, at both timepoints, exhibited normal-appearing neuronal and glial precursors with distinct nuclei and occasional mitotic forms. In sharp contrast, the xenografts containing HIV-$1_{ADA}$-infected monocytes showed significant degeneration at both timepoints. In these grafts, the HIV-1 infected cells had the appearance of activated macrophages with vacuolated cytoplasm. Neurons in close proximity to the infected macrophages were small and dark with fully-defined nuclei indicating cell death. Notably absent were lymphocytes and other inflammatory cells in and around the graft, as is usually seen with transplant rejection. Thus, HIV-1 infected macrophages were specifically-associated with tissue pathology. Further immunohistochemical analysis of representative grafts revealed a proliferation of GFAP positive astrocytes and loss of PGP 9.5 positive neurons immediately adjacent to the HIV-1 infected monocytes within the graft.

DNA prepared from the xenografts and from selected rat and human tissues was analyzed by PCR using primers specific for HIV-1 and host gene sequences. Grafts from one eye of each of the 24 rats from Groups I and II were subjected to PCR analysis individually and compared with other tissues from the same rat as well as with the positive and no DNA controls.

A series of similar experiments demonstrated that in 3 of 16 animals in Groups IA–IE, inoculated after engraftment with concentrated cell-free HIV-1 by multiple routes, HIV-1-specific bands were observed in recovered xenograft tissue. None of the animals from Groups IA or IB had infected grafts, while one graft each from Groups IC, ID and IE gave HIV-1-specific bands. Two of the three infected grafts contained fetal brain tissue, and one had retinal tissue. In Group II animals, in which concentrated HIV-1 was engrafted simultaneously with the neural tissue in the anterior chamber, 5 of 8 xenografts examined by PCR were positive for HIV-1 sequences. Three of these HIV-1-infected grafts were fetal brain tissue and two were fetal retinal tissue. As care was taken to eliminate HIV-1 proviral DNA from the inoculate, the finding of HIV-1 DNA in these experiments is proof of viral replication in xenograft tissue.

Animals in Group III could not be assessed by PCR due to the presence of HIV-1 proviral DNA in the monocytes. Xenografts were studied from these animals by using in situ hybridization. Two grafts from Group III and two grafts from Group II (inoculated with cell-free HIV-1) that were HIV-1 positive by PCR were selected for in situ hybridization and 0.5 μm paraffin sections were prepared. Grafts with neural tissue only and grafts with neural tissue plus uninfected monocytes served as controls. Each graft from HIV-1-inoculated animals contained a small number of macrophages that hybridized to the HIV-1 specific riboprobe. Hybridization occurred with the HIV-1 antisense probe, but not with the sense probe, indicating the presence of HIV-1 RNAS. No hybridization signal was observed in the grafts containing only neural tissue or neural tissue plus uninfected monocytes. In two photomicrographs, the signal was localized over a multinucleated giant cell, similar in appearance to syncytial cells characteristic of HIV-1 encephalitis.

Example 4 Human fetal neuronal grafts in the anterior chamber of CB.17 scid/scid mice Neuronal tissue was introduced into C.B.17 scid/scid mice of about 3 months of age substantially as described in Example 2, except that in a few instances, a 30-gauge butterfly needle was employed, which proved to be less useful than the 27-gauge. The tissue employed was human fetal tissue of about 10–17 week gestation. Two series of mice were implanted with the neural tissue, in the first series the anterior chamber of 10 mice, and in the second series the anterior chamber of 15 mice. One of the mice died in the first series. At the end of 4 weeks after transplantation, 5 of the 9 surviving mice had substantial neural tissue mass in at least one eye. Of the second series, at the end of 4 weeks, 14 of 15 mice had clear clumps of neural tissue in at least one eye.

Histological and immunohistochemical analysis confirm the presence of predominantly neurons with neuritic processes, a fine network of GFAP$^+$ astroglia and occasional RCA-1 lectin$^+$ microglia in these grafts. No evidence of inflammatory reaction or rejection was observed.

The results demonstrate that neuronal tissue will grow in C.B.17 scid/scid mice with high efficiency in obtaining growth in the anterior chamber of the eye.

It is evident from the above results, that neuronal xenografts in the eyes of immunocompromised or immunosuppressed hosts provide for the ability to study human tropic diseases associated with neuronal tissue. Thus, the subject systems allows for the studying not only of the etiology of disease, but also the effect of agents on the disease. Furthermore, the hosts allow for other xenografts, so that the interaction between various foreign tissues, such as migration and differentiation of microglia from bone marrow into the brain, agents acting on the foreign tissues, the effect of agents on a disease unassociated with neural tissue, while studying the effect of the agent on the neural tissue, can now all be examined. The results from these studies may then be used for predicting events in a human host.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An immunocompromised murine host having an HIV infected human fetal neural transplant in the eye, wherein said neural implant is vascularized and has an intact blood brain barrier.

2. A host according to claim 1, wherein said host is a rat treated with an immunosuppressant.

3. A host according to claim 1, wherein said host is a mouse lacking mature B- and T-cells as a result of a genetic lesion.

4. A host according to claim 3, wherein said mouse is a CB.17 scid/scid mouse.

5. An immunocompromised murine chimeric host having a human fetal neural transplant in the eye, wherein said host lacks mature B- and T-cells as a result of a genetic lesion, and wherein said neural implant is vascularized, has an intact blood brain barrier and is capable of being infected with a virus.

6. A host according to claim 5, wherein said host has a second human transplant of tissue other than neural tissue at other than the eye.

7. A host according to claim 6, wherein said second human transplant is lymphoid tissue.

8. A host according to claim 7, wherein said host has circulating human lymphocytes.

9. A host according to claim 5, wherein said human neural transplant is diseased.

10. A host according to claim 9, wherein said diseased human neural tissue is infected with HIV.

11. A host according to claim 5, wherein said host is a mouse.

12. A host according to claim 11, wherein said mouse is a CB.17 scid/scid mouse.

13. A method for determining the effect of an antiviral agent on diseased human neural tissue, said method comprising:

administering said agent to an immunocompromised murine chimeric host having HIV infected human fetal neural transplant in the eye, wherein said neural implants is vascularized and has an intact blood brain barrier; and determining the effect of said agent on said diseased neural tissue.

14. A method for determining the effect of an agent on human neural tissue, said method comprising:

administering said agent to an immunocompromised murine chimeric host having a human fetal neural transplant in the eye, wherein said host lacks mature B- and T-cells as a result of a genetic lesion, has a second human transplant of tissue other than neural tissue at other than the eye, and wherein said neural implant is vascularized and has an intact blood brain barrier; and determining the effect of said agent on said neural tissue.

15. A method according to claim 14, wherein said second human transplant is lymphoid tissue.

16. A method according to claim 15, wherein said host has circulating human lymphocytes or monocytes.

17. A method according to claim 14, wherein said human neural transplant is diseased.

18. A method according to claim 17, wherein said diseased human neural tissue is infected with HIV.

19. A method according to claim 14, wherein said host is a mouse.

20. A method according to claim 19, wherein said mouse is a CB.17 scid/scid mouse.

* * * * *